United States Patent [19]
Fencl et al.

[11] Patent Number: 5,817,276
[45] Date of Patent: Oct. 6, 1998

[54] METHOD OF UV DISTRIBUTION IN AN AIR HANDLING SYSTEM

[75] Inventors: Forrest B. Fencl, Huntington Beach; Robert Scheir, Sherman Oaks; Robert M. Culbert, Manhattan Beach, all of Calif.

[73] Assignee: Steril-Aire U.S.A., Inc., Cerritos, Calif.

[21] Appl. No.: 803,350

[22] Filed: Feb. 20, 1997

[51] Int. Cl.⁶ ..................................................... A61L 2/10
[52] U.S. Cl. ........................... 422/24; 250/455.11; 62/78
[58] Field of Search .......................... 422/121, 24, 186.3; 55/279; 62/78; 250/455.11

[56] References Cited

U.S. PATENT DOCUMENTS

| | | | |
|---|---|---|---|
| 3,744,216 | 7/1973 | Halloran ..................................... | 55/102 |
| 3,926,556 | 12/1975 | Boucher ................................. | 422/24 X |
| 4,245,550 | 1/1981 | Suzuki et al. ............................. | 98/2.11 |
| 4,990,313 | 2/1991 | Pacosz ..................................... | 55/279 X |
| 5,112,370 | 5/1992 | Gazzano ..................................... | 55/102 |
| 5,207,074 | 5/1993 | Cox et al. . | |
| 5,225,000 | 7/1993 | Fujii et al. .................................. | 134/1 |
| 5,326,542 | 7/1994 | Sizer et al. ................................ | 422/291 |
| 5,330,722 | 7/1994 | Pick et al. ................................ | 422/121 |
| 5,334,347 | 8/1994 | Hollander ............................ | 422/121 X |
| 5,453,049 | 9/1995 | Tillman, Jr. et al. .................... | 454/228 |
| 5,492,557 | 2/1996 | Vanella ......................................... | 96/16 |
| 5,523,057 | 6/1996 | Mazzilli ................................... | 422/121 |
| 5,558,158 | 9/1996 | Elmore ................................ | 422/121 X |

*Primary Examiner*—Robert J. Warden
*Assistant Examiner*—E. Leigh McKane
*Attorney, Agent, or Firm*—Steven C. Sereboff; Sereboff & Buyan, LLP

[57] ABSTRACT

A method and apparatus wherein a germicidal lamp's tube is positioned in a particular manner relative to the HVAC system such that the system coil and drain pan components are subjected to UVC radiation and an increased flux density of photons emitted therefrom, and the photons are continuously reflected and directed within and through the coil until absorbed. In this manner the flux density of the photons is increased, as well as the dosage of the photons actually applied to a surface or airborne microorganism, minimizing the occurrence of HVAC-sourced bioaerosols and effectively and efficiently killing the mold and bacteria that grow on the coil and in the drain pan of a HVAC system without producing a secondary contaminant.

14 Claims, 7 Drawing Sheets

METHOD OF UV DISTRIBUTION IN AN AIR HANDLING SYSTEM

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by any one of the patent disclosure, as it appears in the Patent and Trademark Office patent files or records, but otherwise reserves all copyright and trade dress rights whatsoever.

BACKGROUND OF THE INVENTION

1. Field of the Invention

The present invention relates in general to both surface and air sterilization, and more particularly to a method and an apparatus for the distribution and substantially increased space flux density of photons generated and applied to a coil and drain pan as utilized in heating, ventilating and air conditioning (HVAC) systems, and the surrounding space in which such an apparatus is housed, and to focus the dosage of irradiation applied to any airborne organism carried thereon and therein.

2. Description of Related Art

The use of electric discharge devices for air sterilization by germicidal tubes, is well known to those skilled in the art, but the functional implementation of such devices in HVAC equipment has been limited. Various reasons have contributed to the lack of success in the utilization of electrical discharge devices for this purpose, such as the physical characteristics of the plasma gases and partial pressure thereof from which the devices are constructed, the electrical characteristics required to excite these materials as contained within the envelope in order to emit ultraviolet radiation, with sufficient internal heat generated by the power applied to the gases in order to prevent insufficient plasma temperature, thus output, in a cold temperature environment. In addition, when such discharge devices are used to sterilize a moving air stream, the air moving across the tube envelope lowers the plasma temperature inside the envelope such that the emission of the ultraviolet radiation decreases at a rapid rate—as much as a 75% degradation in a conventional tube—when the temperature falls below 58° F. This phenomenon, referred to as "skin-effect cooling," increases the number of conventional tubes required to obtain a predetermined ultraviolet irradiance level, reduces the available square area for airflow thus reducing air changes per hour (ACH), and increases the number of expensive tube replacements. As is known to those skilled in the art, germicidal tubes emit ultraviolet light at the primary and secondary emission lines of mercury—254 nm and 185 nm.

At mercury's secondary emission line 185 nm and below, large amounts of ozone are created. Ozone must be strictly controlled because of its harm to humans and its known carcinogenic effect. Despite the clear benefits of germicidal lamps, problems such as ozone, depressed output in low temperatures and short tube life have prevented their use in all but highly specialized applications.

For further information concerning improvements in electrical discharge devices which are directed to overcoming such problems, reference is made to B. C. Hollander U.S. Pat. No. 5,334,347, "ELECTRIC DISCHARGE DEVICE," and a pending application filed in the name of two of the instant inventors, Forrest B. Fencl and Robert M. Culbert, entitled "SINGLE-ENDED GERMICIDAL LAMP," Ser. No. 08/773,463 the disclosures of which are incorporated herein by reference.

One area which has long sought to use germicidal lamps is the HVAC industry. HVAC systems typically comprise fans and ducts for moving air where needed. An HVAC system may also include a cooling section and a heating section for, respectively, cooling and heating the air. In most systems, air is drawn in, filtered, cooled or heated, humidified, and then delivered to a room. Air is also drawn from the room for recirculation through the HVAC system.

The HVAC industry has adapted standards for the rate of air exchange (ACH) in a room, as well as standards for introduction of fresh air into the spaces serviced by an otherwise closed HVAC system. Such spaces include offices, living spaces, commercial spaces, industrial spaces and institutional spaces, as well as the interior of vehicles such as cars, buses, planes and ships. The HVAC systems deliver air which is specifically of a temperature, humidity and flow rate that is detrimental to conventional germicidal lamp operation for the reasons explained above. The frequent changes of temperature, humidity and flow rate required to control the comfort level and indoor air quality (IAQ) of the air in these various spaces destabilizes the operation of conventional germicidal lamps. In addition to controlling the IAQ for occupant comfort, often the goal of HVAC systems is to provide air free from injurious microorganisms, be it for semiconductor or pharmaceutical and food processing facilities, hospitals, schools, offices or homes.

Because of the existence and growth of molds and bacteria which occur at the cooling section of the HVAC system, and the ability of the system to recirculate infectious disease organisms, additional fresh air, for dilution, is necessarily introduced into the system thereby decreasing system efficiency. Degradation of IAQ, or spread of infectious disease caused by such microorganisms, can result from HVAC sourced and recirculated bioaerosols. Poor IAQ and the spread of such infectious disease can reduce worker productivity and increase absenteeism. In addition, when mold and bacteria are permitted to grow on the coil, and in the drain pans of an HVAC system, equipment maintenance problems occur which are very costly to correct. If such maintenance problems are not corrected, these problems are exacerbated and eventually system heat transfer efficiency will decrease.

One attempt to control the formation and growth of such microorganisms, is through the use of liquid biocidal agents which are applied to the surfaces of the HVAC apparatus. However, the application of such liquids requires the use of potentially dangerous chemicals, the application of which is strictly controlled by the licensing by the EPA of those who supply and apply such materials requiring such persons to use masks and gowns when performing such applications. Such chemical coating processes should also require the vacating of the building while the HVAC system is being treated, and may only be effective for as short a period as from three days to three weeks. In order to control airborne infectious disease organisms, high efficiency particulate arrester (HEPA) filters, and the installation of ultraviolet radiation discharge devices, are utilized. The installation and maintenance of HEPA filters is very costly.

SUMMARY OF THE INVENTION

It is, therefore, an object of this invention to minimize the occurrence of HVAC sourced bioaerosols and, therefore, to improve air quality, maintenance and occupant health in an efficient and effective manner.

A further object of this invention is to effectively and efficiently kill the mold and bacteria that through system design evolution, more typically grow on the coil and in the drain pan of an HVAC system on a continuous basis. It is a further object to do so without producing any secondary contaminant Still another object of this invention is to eradicate the metabolites, mycotoxins, endotoxins and cell fragments which are a by-product of mold and bacterial growth occurring on the coil and in the drain pan.

Yet another object of this invention is to utilize the HVAC system coil as a UV reflection labyrinth and flux density enhancer to accomplish these objectives as well as the objective of killing airborne infectious disease organisms and thus the requirement for additional outdoor air needed for dilution.

The present invention defines a method and utilizes a germicidal tube which is positioned in a particular manner relative to the HVAC system such that the coil and drain pan components and surfaces are all subjected to irradiance and an increased flux density of the photons emitted therefrom. Photons are continuously directed and reflected within and through the coil until absorbed. In this manner the flux density of the photons is increased, and likewise, the dosage of the photons actually applied to a surface or airborne microorganism. Thus eradicating drain pan microorganisms and their products and odors, a portion of airborne infectious organisms, while reducing the amount of additional outdoor air needed for dilution.

These and other objects are attained in accordance with the present invention wherein there is provided an electrical discharge device, a germicidal lamp, which is positioned in a particular manner relative to an HVAC system to provide a method of subjecting the system coil and drain pan components to an increased flux density of the photons emitted therefrom, so that the photons are continuously reflected and directed within and through the coil until absorbed. In this manner the flux density of the photons is increased, as well as the dosage of the photons actually applied to a surface or airborne microorganism.

DESCRIPTION OF THE DRAWINGS

Further objects of the invention, together with additional features contributing thereto and advantages accruing therefrom, will be apparent from the following description of a preferred embodiment of the present invention which is shown in the accompanying drawings with like reference numerals indicating corresponding parts throughout and which is to be read in conjunction with the following drawings, wherein.

These and additional embodiments of the invention may now be better understood by turning to the following detailed description of the invention wherein the illustrated embodiments are described.

DETAILED DESCRIPTION OF THE INVENTION

Throughout this description, the preferred embodiment and examples shown should be considered as exemplars, rather than limitations on the apparatus and methods of the present invention.

Figure 1:
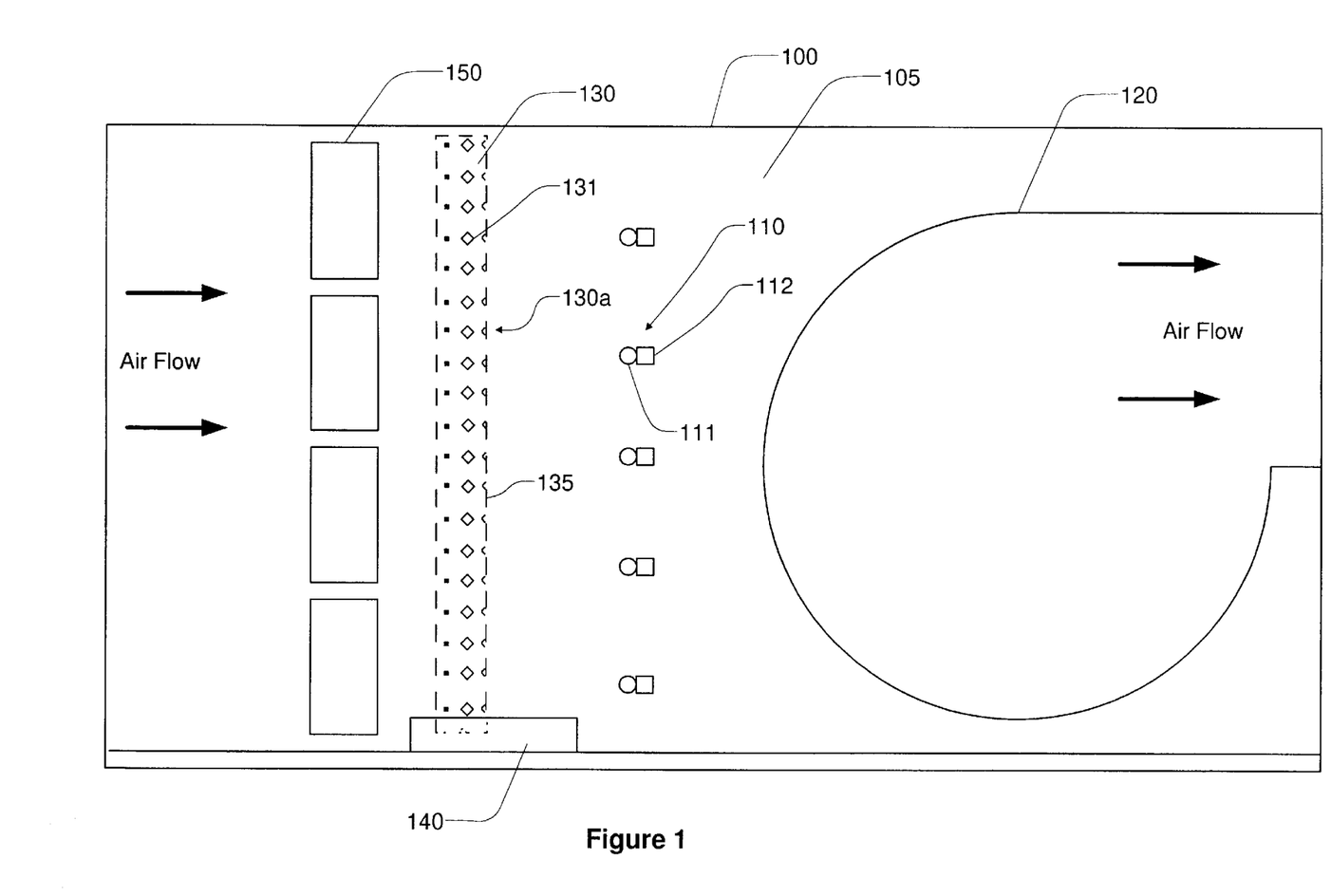
FIG. 1 is a diagrammatic side elevational view of a part of an HVAC system illustrating the positioning of the germicidal tube relative to a heat transfer coil and a drain pan.

Referring now to FIG. 1, there is shown an air duct 100 of an HVAC system, through which conditioned air is discharged in accordance with the operation of a suitable blower or fan 120. A number of germicidal lamps 110 are mounted in a chamber 105 of the air duct 100. The germicidal lamps 110 include a germicidal tube 111 coupled to and carried by a base 112. For the germicidal lamps to operate effectively in the harsh environs of an air duct, it is preferred that germicidal lamps specifically designed for such environments be employed. In particular, the germicidal lamps sold by the assignee of this invention, Steril-Sir U.S.A., Inc, and sold under the trademark, "UVC Emitter," are preferred. The base 112 contains electrical circuitry and ballast for energizing the germicidal tube 111 to emit ultraviolet radiation, preferably in the "C" band (UVC). Although not shown in FIG. 1, there may be a number of single-ended germicidal tubes coupled to a single base, with the base mounted on the outside of the duct 100. Such a configuration is disclosed in the co-pending application referred to above, "SINGLE-ENDED GERMICIDAL LAMP." Other configurations of germicidal tubes and bases are within the scope of the invention.

A horizontal flow, flat heat transfer coil 130 and drain pan 140 of the HVAC system are positioned adjacent to the chamber 105, preferably upstream from the germicidal lamp 110 with reference to the air flow. While this is the preferred positioning, it is to be understood that the lamp 110 may also be positioned upstream from the coil 130 and drain pan 140, whichever provides good uniform radiation coverage of the coil 130 and drain pan 140 and best accommodates the HVAC system's layout.

The coil 130, which is well known in the art, comprises circuited tubes 131 through which coolant circulates and a number of substantially flat, planar parallel fins 135 attached at generally regular spaces on the tubes 131. The relationship between the coil tubes 131 and the fins 135 can be better appreciated from FIG. 3. The fins 135 increase the effective surface area of the tubes 135 to thereby increase heat transfer from the coolant to air passing over the coil 130. Because of the excellent heat transfer properties, low expense and ease of manufacture of aluminum, a typical coil is substantially constructed of this material. In general, for heat transfer, cost and manufacturing reasons, the fins 135 are rarely coated. Coincidently, aluminum has in excess of 60% reflectivity for the primary UV emission line, a wavelength of 253.7 nm. However, the method of the invention is also applicable to fins of other materials which are relatively good reflectors of UV's primary emission line.

Further upstream from the coil 130 are a number of filters 150.

Figure 2:
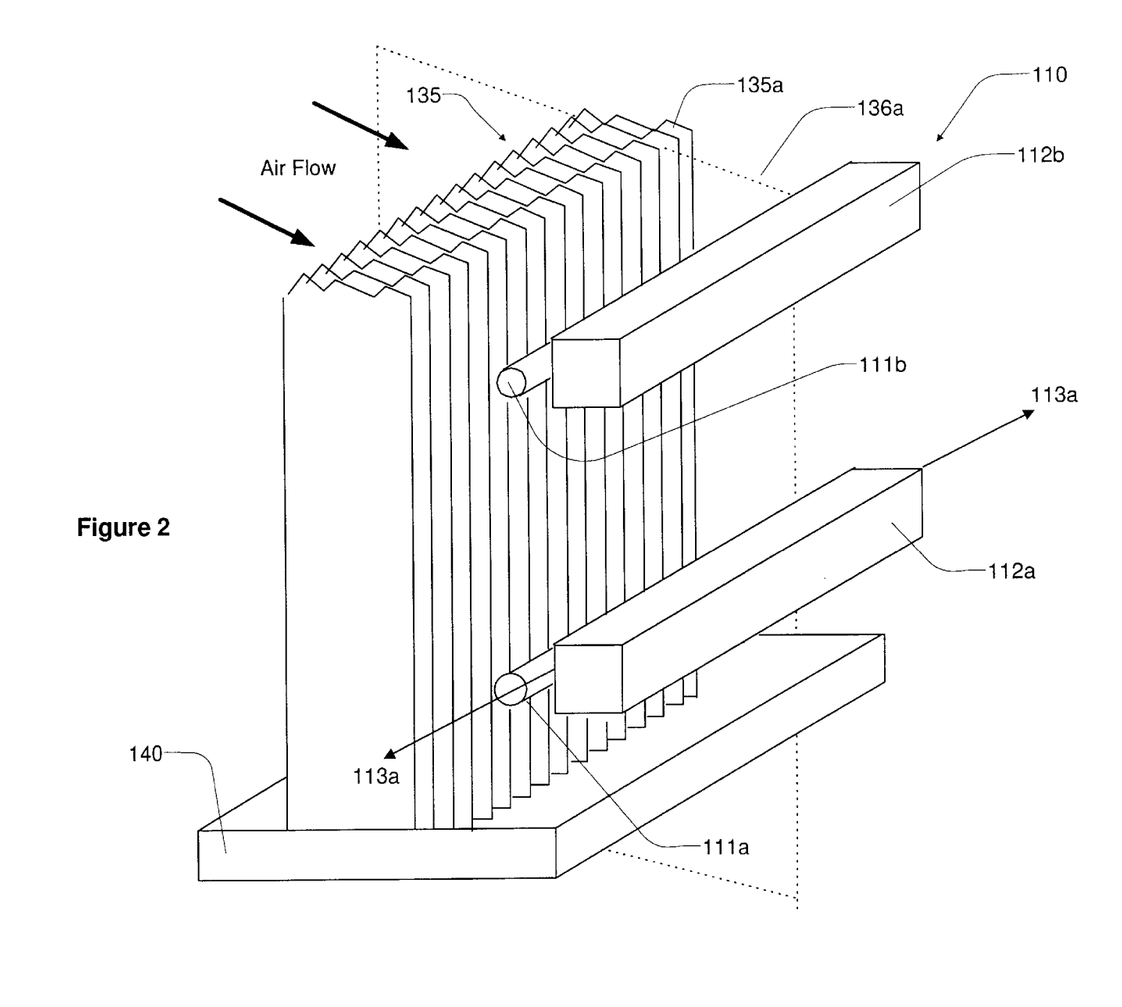
FIG. 2 is a diagrammatic perspective elevational view of a horizontal flow flat heat transfer coil to illustrate the positioning of germicidal tubes relative of the coil's heat transfer fins.

Referring now to FIG. 2, there is shown a diagrammatic perspective view of the fins 135 and the germicidal lamps 110. For a given fin 135a, there is defined a plane 136a of the fin 153a. For a given germicidal tube 111a, there is defined a longitudinal axis 113a. Preferably, the longitudinal axis 113a of the germicidal tube 111a is at a right angle to the plane 136a of the fins 135a. Since the fins 135 are parallel and vertical, the germicidal tubes 111 will be at right angles and horizontal to the plane of all of the fins 135.

Figure 3:
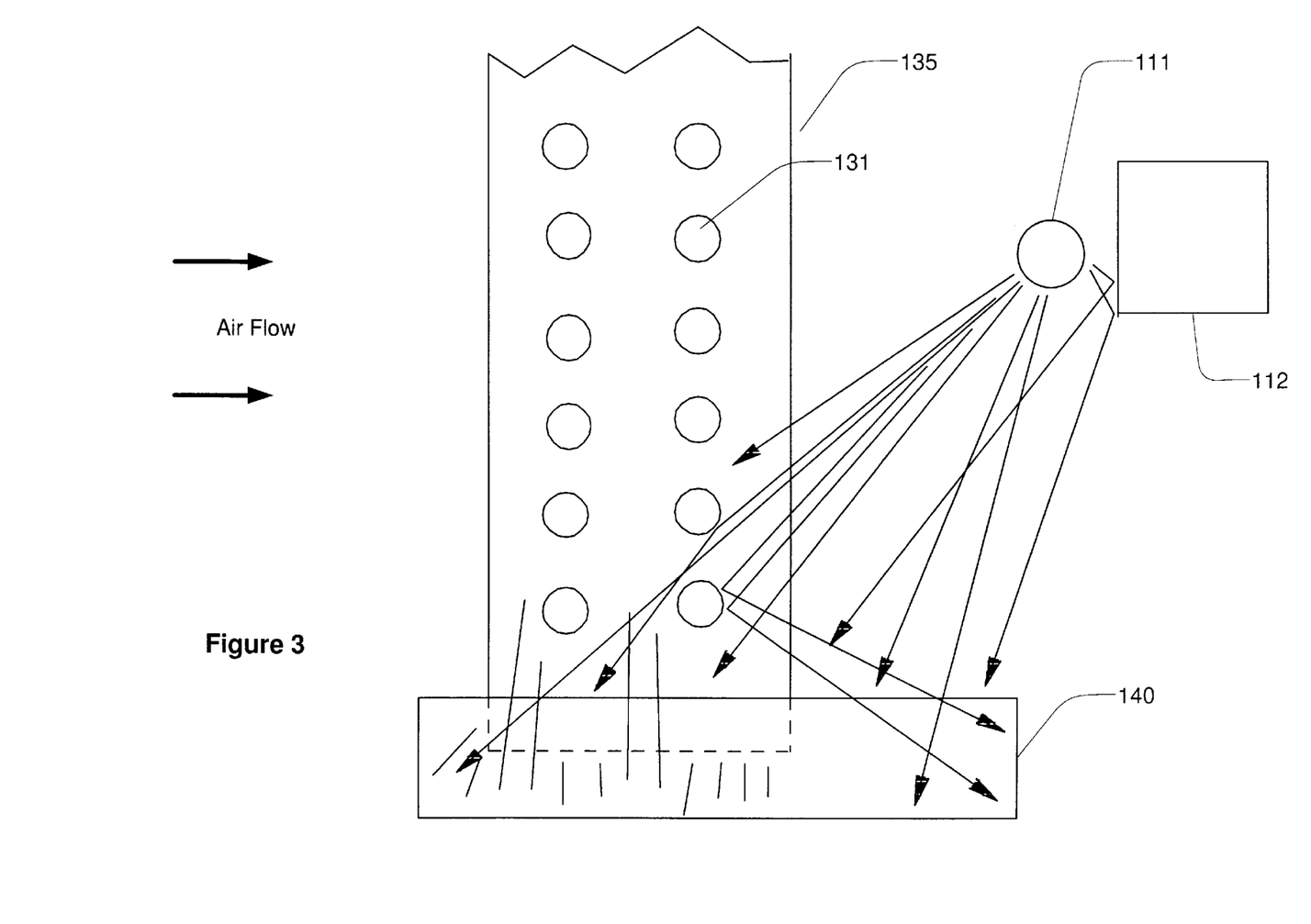
FIG. 3 is a diagrammatic elevational illustration of a portion of the cross section of the horizontal flow flat heat transfer coil illustrated in FIG. 2 to better illustrate the manner in which the germicidal tube is positioned adjacent to the coil and drain pan perpendicular to the parallel planes of the coil illustrating the manner in which UV radiation is applied thereto.

Referring now to FIG. 3, it can be seen that at least one germicidal tube 111 is also positioned so as to irradiate at least part of the drain pan 140. In accordance with the invention, the coil's tubes 131 also act as a mirror for UV radiation from the germicidal tube 111. The fins 135 also reflect UV radiation onto the drain pan 140. Accordingly, the surface of the drain pain 140 will also be irradiated through reflections of the UV radiation from the tubes 131.

Figure 4:
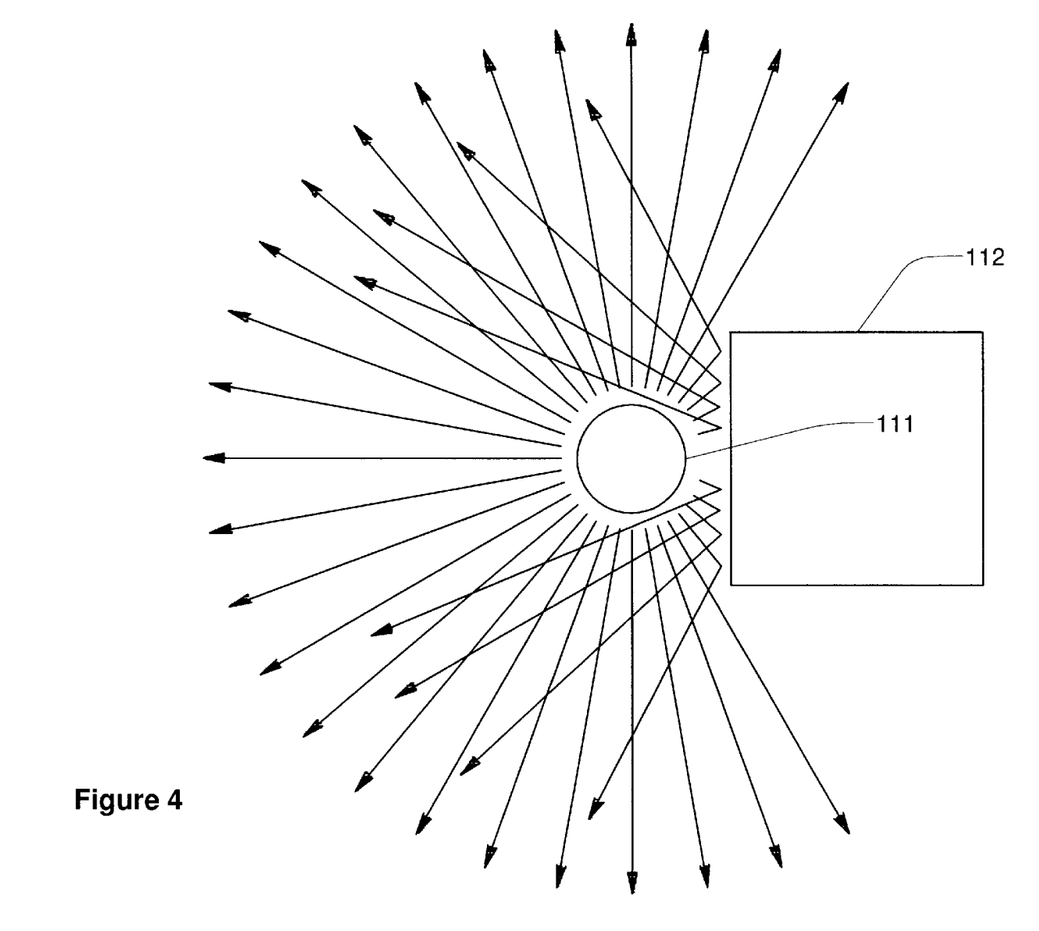
FIG. 4 is a diagrammatic elevational representation of a germicidal tube taken in a plane perpendicular to the longitudinal axis of the germicidal tube and parallel to the plane of an adjacent heat transfer coil to illustrate radiation emitted from the germicidal tube in that plane.

In determining the spatial relationship between the germicidal tubes 111 and the coil 130 (FIG. 1), the objective is to obtain a uniform distribution of UV radiation across the coil's face 130a. (The coils' face 130a also substantially defines the leading edge of the fins 135.) It has been determined that, for a germicidal tube which is positioned in accordance with the invention, the spatial distribution of UV radiation follows precisely that of a diffuse area source and, surprisingly, not an isotropic point source. The pattern of UV radiation from a germicidal lamp is shown in FIG. 4. It can be seen that although the germicidal tube 111 is a source of irradiation, the base 112 is effectively a secondary source of UV radiation. The energy distribution of the germicidal tubes 111 is therefore defined as a near field effect, not as an inverse square law. This finding is contrary to normal expectations, and therefore placement of germicidal tubes in accordance with the present invention results in the need for fewer germicidal tubes. Put another way, when the germicidal tubes 111 are positioned sufficiently closely to the coil 130, the intensity of UV radiation from the germicidal tubes 111 striking the coil 130 is, to a degree, independent of the distance of the germicidal tubes 111 from the coil 130.

In one embodiment of the invention, germicidal tubes, spaced 24 inches apart, were positioned at right angles to the plane of the fins and about twelve inches from the drain pan and twenty inches from the face of the coil. It has been found that positioning the germicidal tubes 111 20 inches from the leading edge 130a of the fins 135, in conjunction with appropriate germicidal tube-to-tube spacing, is particularly effective in inhibiting the growth of microorganisms on all surfaces of the coil 130 and in all surface areas of the drain pan 140.

As shown in FIG. 4 the photons emitted from a particular point on the germicidal tube 111 radiate in all directions. Because FIG. 4 is an elevational view, the global radiation of these photons is not shown. These photons would, however, radiate outwardly and inwardly from the plane of the paper upon which the planar representation is illustrated. In addition, to increase the photons applied to the coil and drain pan, a germicidal lamp with a reflector (preferably incorporated in the base 112) is utilized. Those photons emitted in a plane parallel to the planes of the fins 135 penetrate into the coil 130 and are reflected by the internal coil structure (i.e., the tube 131 and the fins 135).

Figure 5:
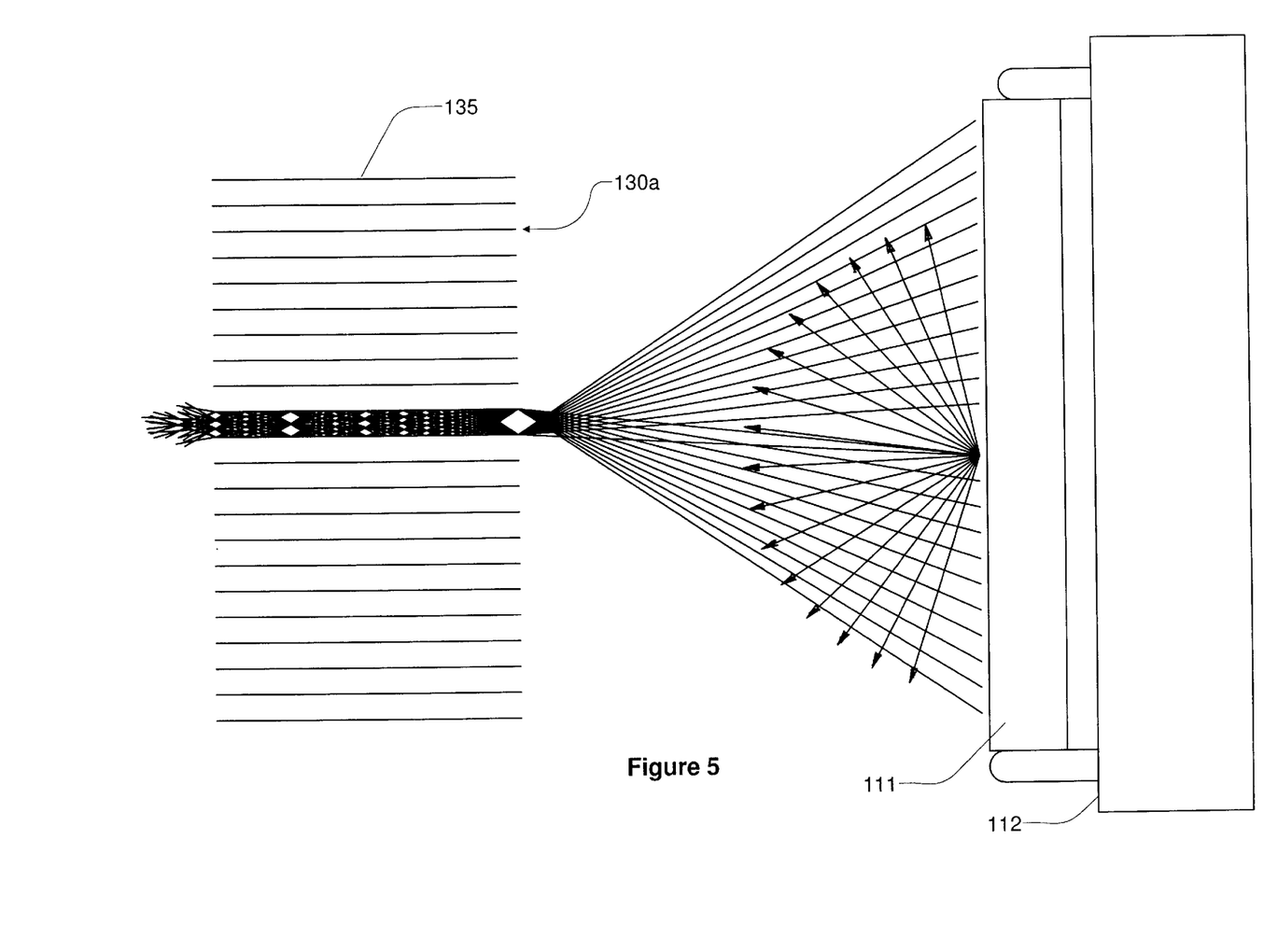
FIG. 5 is a diagrammatic planar representation of UV radiation emitted from the germicidal tube illustrated in FIG. 4 taken in a plane parallel to the longitudinal axis of the lamp and perpendicular to parallel planes of the heat transfer fins to illustrate the directing and reflecting of UV radiation from all points of the lamp in that plane will be applied between adjacent vertical planes of the heat transfer fins, and the manner in which a particular point on the tube will radiate photons in the direction of the fins to increase flux density and dosage applied thereto.
Figure 6:
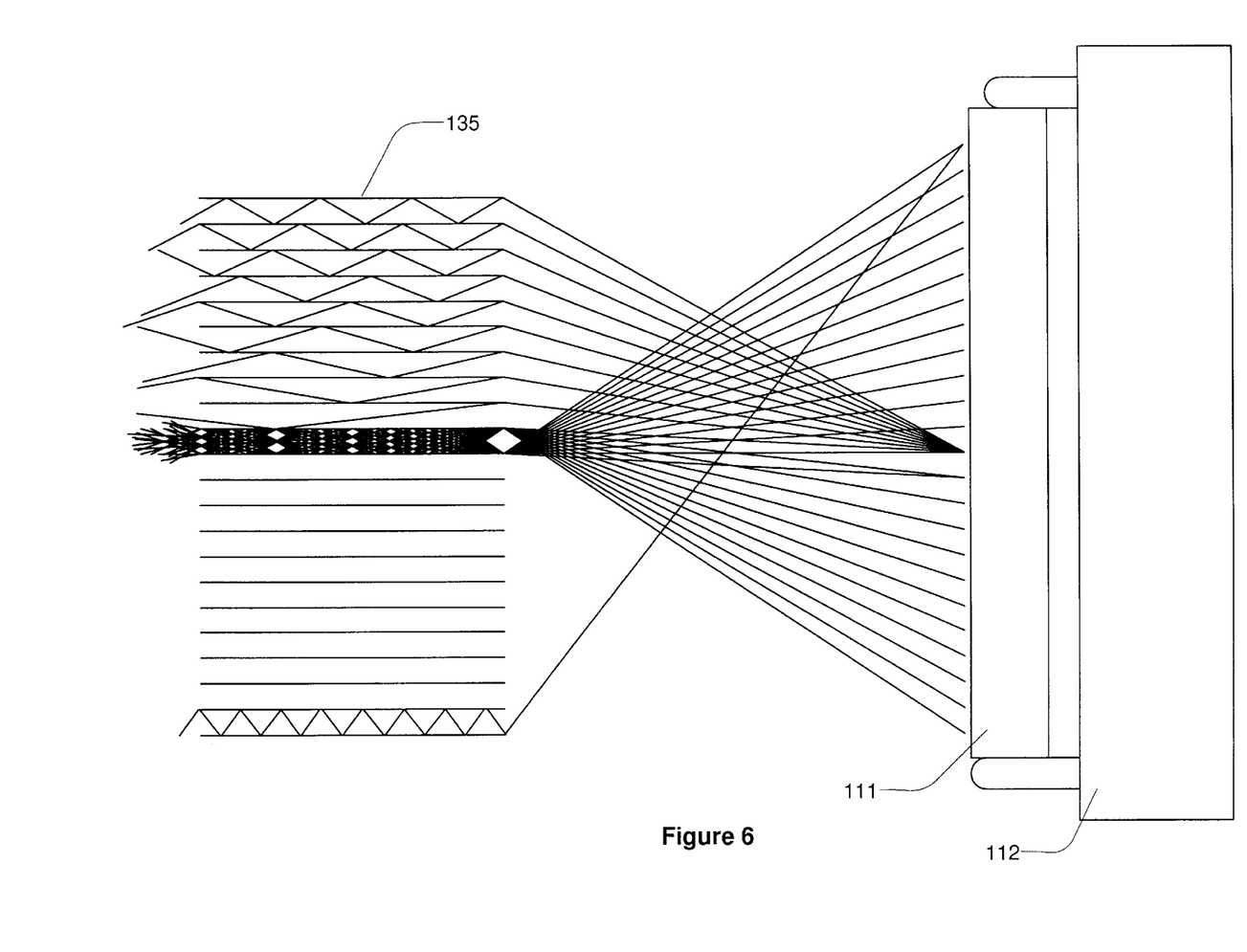
FIG. 6 is a diagrammatic planar representation as in FIG. 5 illustrating the manner in which the UV radiation from all points of the germicidal tube in that plane will be applied between each pair of adjacent parallel planes of the fins, and the manner in which the radiation from a particular point on the germicidal tube will be received and reflected between all of the parallel fins of the coil's tubes for a better understanding of how the radiated energy and subsequent irradiance of that energy is focused and thus enhanced.

As illustrated in FIG. 5 and 6, because of the global emission of photons from the germicidal lamp, photons emitted from all points on the germicidal lamp, other than those emitted in a plane parallel to the planes of the fins 135 strike the fins 135 adjacent to their leading edge 130a (the edge closest to the germicidal lamp 110) are reflected between the spaced parallel fins 135 in accordance to the angle of incidence that the photon takes. The fins 135 and coil 131 therefore reflect photons amongst one another such that the photons are applied throughout the coil 130 and the drain pan 140. Because the global emission occurs from all points along the longitudinal axis 113a of the germicidal tube 111, the flux density and uniformity of incidence to the fins 135, the coil tube 131 and the drain pan 140 increases in the manner diagrammatically illustrated by the reflectivity shown occurring between a pair of fins 135 in each of these Figures. Such increased flux density and dosage occurs between all of the spaced parallel fins 135 in this manner. However, for purposes of illustration, such increases are shown in FIG. 5 occurring between only two adjacent fins.

As can be seen from these Figures, complete and uniform irradiation is achieved. Preferably, the number and position of germicidal tubes is selected so that the UV radiation is uniformly distributed across the coil 130.

Figure 7:
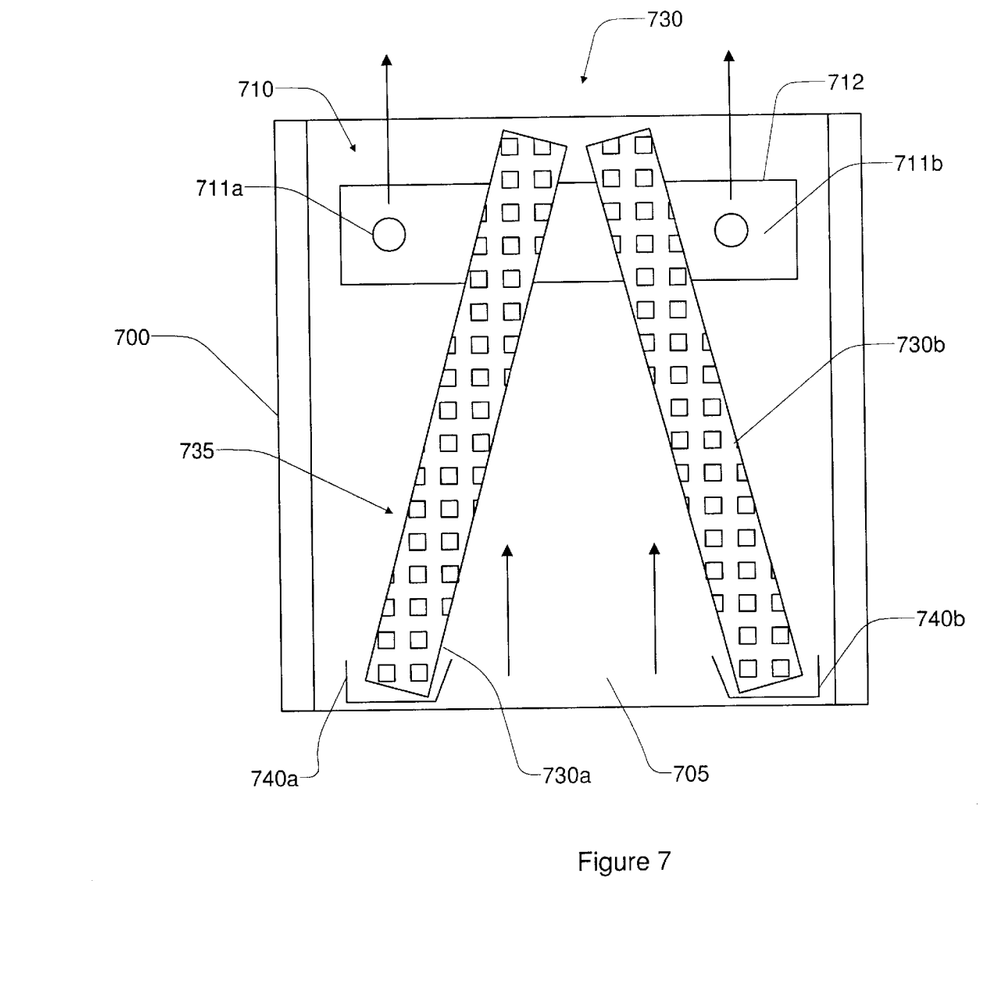
FIG. 7 is a diagrammatic illustration of the cross section of a residential "A" coil to illustrate positioning of a germicidal tube relative to the coil's fin in accordance with one aspect of the invention.

Referring now to FIG. 7, there is shown a diagrammatic illustration of the cross section of a vertical flow A heat transfer coil 740 to illustrate positioning of germicidal tubes 711a, 711b relative to the coil's fins in accordance with one aspect of the invention. The germicidal tubes 711a, 711b, in base 712, are positioned at right angles to the planes in which the fins 735 lie. The germicidal tubes 711a, 711b will also partially directly irradiate the drain pans 740a, 740b, while the coil 730 will cause indirect irradiation of the drain pans 740a, 740b in the manner described above.

It has been determined that positioning the germicidal tubes such that their longitudinal axes are perpendicular to the parallel planes in which the fins extend causes the emitted UV radiation to be applied directly to the coil and surrounding areas in the path of emission, and to the drain pan. The actual positioning of the germicidal tubes, and the number of germicidal tubes to be employed in order to attain these objectives, is determined based on the goal that the UV radiation is uniformly distributed across the coil.

Because the UV radiation impinges on the fins at all incident angles, the fins continuously reflect and effectively direct the UV radiation within and through the coil. This continuous reflection and direction of the UV radiation increases the flux density of the photons applied to the coil, the drain pan and continues in the airstream until absorbed. The increased number (flux density) of incident angled photons also assures that organisms in the airstream are struck from all angles. Also, the increased distance of photon travel, and thus available time of exposure, provides for a potentially greater dosage (intensity multiplied by time) to be received by any surface or airborne microorganism. In this manner the coil, drain pan and surrounding area are completely exposed to the UV radiation sufficiently to eradicate surface and substantially reduce airborne microorganisms.

While this invention has been described in the specification and illustrated in the drawings with reference to preferred embodiments, the structures of which have been disclosed herein, it will be understood by those skilled in the art to which this invention pertains that various changes may be made and equivalents may be substituted for elements of the invention without departing from the scope of the claims. Therefore, it is intended that the invention not be limited to the particular embodiments disclosed in the specification and shown in the drawings as the best mode presently known by the inventors for carrying out this invention, nor confined to the details set forth, but that the invention will include all embodiments, modifications and changes as may come within the scope of the following claims.

It is claimed:

1. A method of controlling the presence of surface and airborne carried microorganisms in an air treatment apparatus having a drain pan and a heat transfer coil comprising a tube and a plurality of spaced parallel fins, comprising the steps of:

positioning a substantially linear germicidal tube adjacent to the coil and drain pan of an air treatment apparatus with the longitudinal axis of the germicidal tube being aligned in a position substantially perpendicular to the parallel planes of the fins;

energizing the germicidal tube to emit substantially uniformly distributed UV radiation across the coil face to the coil's tube and fins and the drain pan;

reflecting and directing the UV radiation by the coil's tube and the fins throughout the coil, thereby increasing the flux density of the UV radiation and the dosage of the radiation applied to airborne microorganisms and microorganisms carried on the surfaces of the coil and drain pan.

2. The method of claim 1 wherein said reflecting and directing of the UV radiation received by the coil, the fins and the drain pan is effected by the reflectivity of UV radiation from the materials from which the coil, the coil and the drain pan are fabricated, thereby increasing the flux density of said radiation.

3. The method of claim 2 wherein said reflecting and directing of the UV radiation reflected from said coil, said fins and said drain pan components continues until said radiation is absorbed, thereby increasing the dosage of radiation applied to said components.

4. In an air conditioning system wherein a substantially linear germicidal tube is positioned within the air stream to emit UV radiation for controlling the presence of microorganisms in the air conditioning system, said air conditioning system including a heat transfer coil having a plurality of parallel spaced fins and a drain pan, the improvement comprising:

positioning said substantially linear germicidal tube adjacent to said heat transfer coil and said drain pan in a position with the longitudinal axis of the germicidal tube being aligned substantially perpendicular to the parallel planes of said fins to emit substantially uniformly distributed UV radiation across the face of said coil such that the UV radiation received by said coil, said fins and said drain pan is reflected and directed throughout the coil, the fins and the drain pan to thereby increase the flux density of the UV radiation and the dosage of the UV radiation applied to airborne and surface microorganisms carried therein and thereon.

5. In an air conditioning system including a heat transfer coil, and a blower or fan for generating an air flow through the system, said heat transfer coil including a plurality of spaced parallel fins and an adjacent drain pan, the improvement comprising:

a substantially linear germicidal tube positioned downstream of and adjacent to said coil and said drain pan of said air conditioning system in a position with the longitudinal axis of the germicidal tube being aligned substantially perpendicular to the parallel planes of said fins for emitting substantially uniformly distributed UV radiation across said coil face such that the emitted UV radiation is reflected and directed throughout said coil, said fins and said drain pan to increase the flux density of the UV radiation and the dosage of the UV radiation applied to airborne and surface microorganisms carried on and in said air conditioning system.

6. A method of controlling the presence of surface and airborne carried microorganisms in an air treatment apparatus having a heat transfer coil comprising a tube and a plurality of spaced parallel fins, comprising the steps of:

positioning a substantially linear germicidal tube adjacent to the coil of the air treatment apparatus with the longitudinal axis of the germicidal tube being aligned in a position substantially perpendicular to the parallel planes of the fins;

energizing the germicidal tube to emit substantially uniformly distributed UV radiation across the coil face to the coil's fins;

reflecting and directing the UV radiation by the coil's fins throughout the coil, thereby increasing the flux density of the UV radiation and the dosage of the radiation applied to airborne microorganisms and microorganisms carried on the surfaces of the coil.

7. The method of claim 6 wherein said reflecting and directing of the UV radiation received by the fins is effected by the reflectivity of UV radiation from the materials from which the fins are fabricated, thereby increasing the flux density of said radiation.

8. The method of claim 7 wherein said reflecting and directing of the UV radiation reflected from said fins continues until said radiation is absorbed, thereby increasing the dosage of radiation applied.

9. In an air conditioning system wherein a substantially linear germicidal tube is positioned within the air stream to emit UV radiation for controlling the presence of microorganisms in the air conditioning system, said air conditioning system including a heat transfer coil having a plurality of parallel spaced fins, the improvement comprising:

positioning said substantially linear germicidal tube adjacent to said heat transfer coil in a position with the longitudinal axis of the germicidal tube being aligned substantially perpendicular to the parallel planes of said fins to emit substantially uniformly distributed UV radiation across the face of said coil such that the UV radiation received by said coil and said fins is reflected and directed throughout the coil and the fins to thereby increase the flux density of the UV radiation and the dosage of the UV radiation applied to airborne and surface microorganisms carried therein and thereon.

10. The improvement of claim 9 wherein said reflecting and directing of the UV radiation received by the fins is effected by the reflectivity of UV radiation from the materials from which the fins are fabricated, thereby increasing the flux density of said radiation.

11. The improvement of claim 10 wherein said reflecting and directing of the UV radiation reflected from said fins continues until said radiation is absorbed, thereby increasing the dosage of radiation applied.

12. In an air conditioning system including a heat transfer coil, and a blower or fan for generating an air flow through the system, said heat transfer coil including a plurality of spaced parallel fins, the improvement comprising:

a substantially linear germicidal tube positioned downstream of and adjacent to said coil of said air conditioning system in a position with the longitudinal axis of the germicidal tube being aligned substantially perpendicular to the parallel planes of said fins for emitting substantially uniformly distributed UV radiation across said coil face such that the emitted UV radiation is reflected and directed throughout said coil and said fins to increase the flux density of the UV radiation and the dosage of the UV radiation applied to airborne and surface microorganisms carried on and in said air conditioning system.

13. The improvement of claim 12 wherein said reflecting and directing of the UV radiation received by the fins is effected by the reflectivity of UV radiation from the materials from which the fins are fabricated, thereby increasing the flux density of said radiation.

14. The improvement of claim 13 wherein said reflecting and directing of the UV radiation reflected from said fins continues until said radiation is absorbed, thereby increasing the dosage of radiation applied.

* * * * *